United States Patent [19]

Vining et al.

[11] Patent Number: 4,507,117
[45] Date of Patent: Mar. 26, 1985

[54] SYRINGE APPARATUS WITH RETRACTABLE NEEDLE

[76] Inventors: Herbert C. Vining, R.R. 1, Box 339 HV; Clara G. Ryan, R.R. 1, Box 399 FG, both of Patterson, La. 70392

[21] Appl. No.: 512,272

[22] Filed: Jul. 11, 1983

[51] Int. Cl.³ .............................................. A61M 5/22
[52] U.S. Cl. ..................................... 604/196; 604/228
[58] Field of Search ............... 604/194, 196, 191, 228, 604/229, 231, 218, 197, 195

[56] References Cited

U.S. PATENT DOCUMENTS

| 2,888,923 | 6/1959 | Reis | 604/194 |
|---|---|---|---|
| 3,356,089 | 12/1967 | Francis | 604/197 X |
| 3,487,834 | 1/1970 | Smith, Jr. et al. | 604/197 |
| 3,527,216 | 9/1970 | Snyder | 604/196 X |

Primary Examiner—J. Yasko
Attorney, Agent, or Firm—Bode & Smith

[57] ABSTRACT

A syringe apparatus having a syringe barrel open-ended on a first end for receiving a piston therewithin for movement down the syringe barrel, and having on the second end a constricted neck portion with a bore therethrough in communication with the bore within the syringe barrel. There would be further provided a needle portion having an upper base for mounting the upper portion of the needle, with the needle slidable within the bore of the constricted neck portion, from a position retracted into the neck portion to a position movable out of the end of the neck portion for injection. There is further provided a first and second locking members. The first locking member allows locking engagement between the slidable piston within the barrel and the lower base portion of the needle, so that when in the locked position the needle moves in relation with the piston portion. There is further provided a second locking member between the needle portion and the constricted neck portion of the barrel, so that the needle may be locked into injection position, i.e., the needle extruding out of the neck portion during use. Following the injection, the needle can be unlocked from the constricted neck portion and retracted back into the barrel for disposal, thus eliminating the hazard of an exposed contaminated needle, further extraction of the plunger portion from the syringe prior to disposal of same.

8 Claims, 11 Drawing Figures

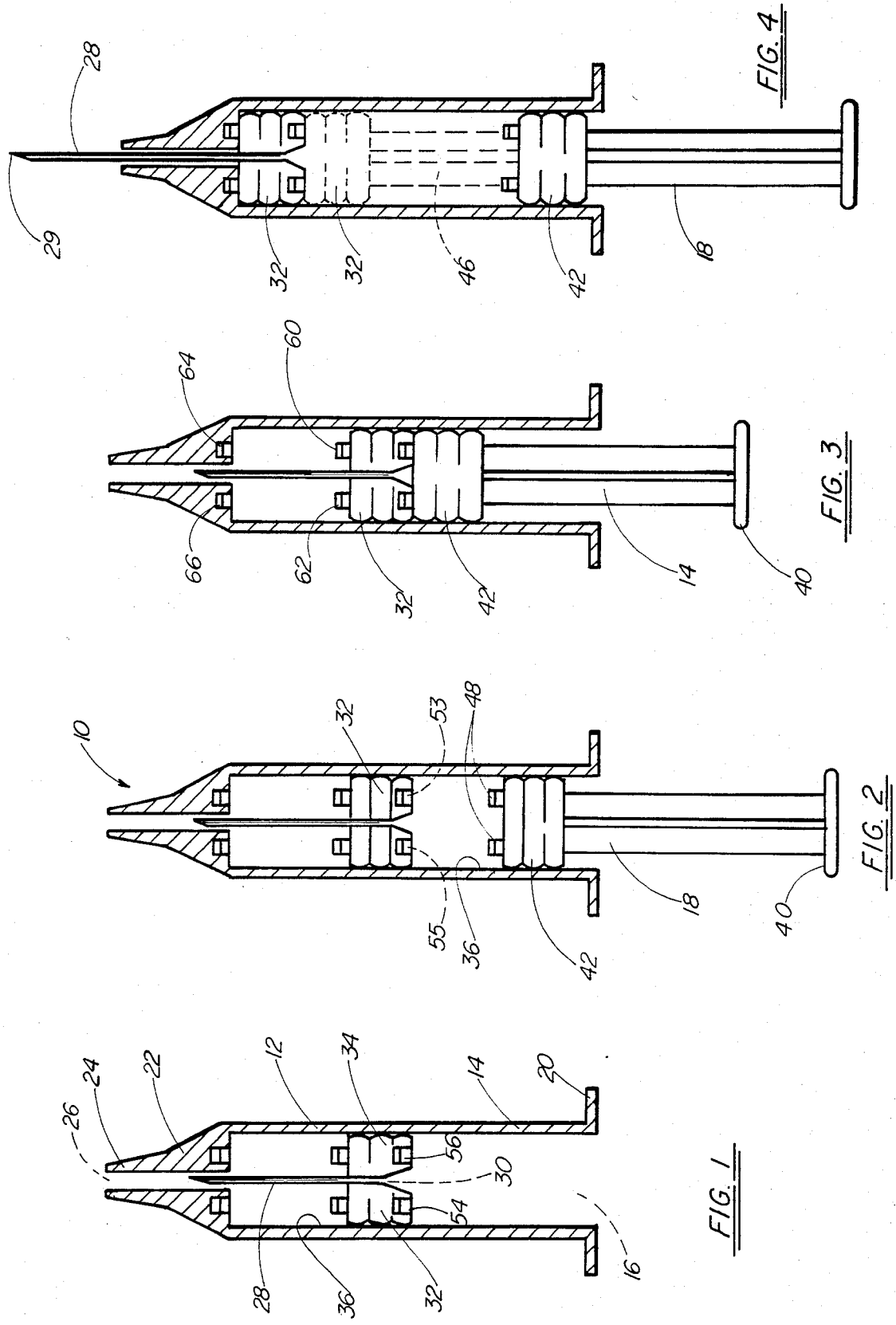

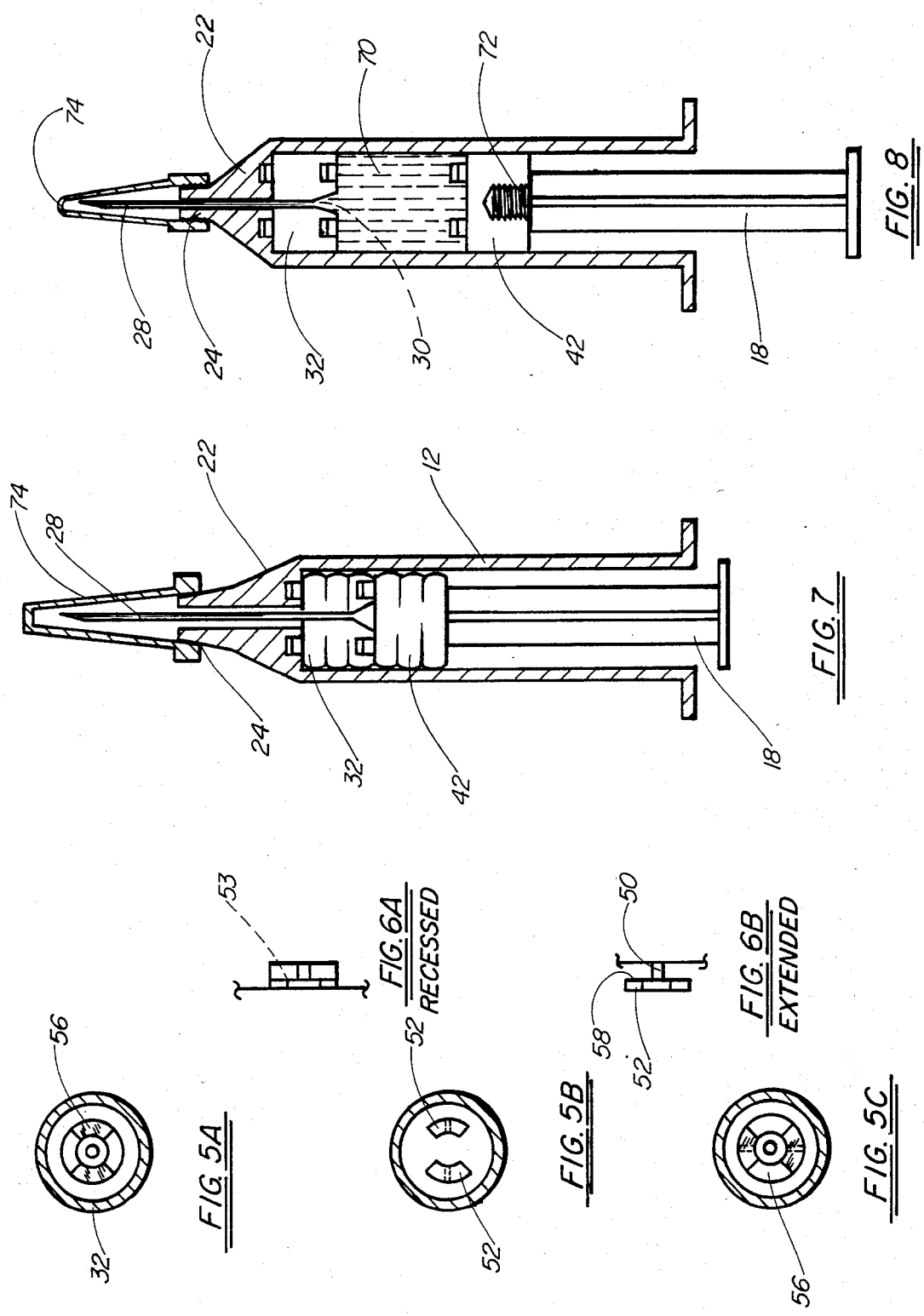

SYRINGE APPARATUS WITH RETRACTABLE NEEDLE

BACKGROUND OF THE INVENTION

1. Field of the Invention

The apparatus of the present invention relates to syringes. More particularly, the apparatus of the present invention relates to a hypodermic syringe having a needle portion retractable both prior to and following the injection.

2. General Background

In the general area of hospital care and treatment of patients, one of the most troublesome areas which confronts hospital staff and personnel, particularly individuals who administer medications parenterally, are the preventive measures which are utilized to combat needle-stick injuries.

A common problem in the area, is following the utilization of a needle with the typical hypodermic syringe which contains a needle extruding permanently from the syringe, is the risk of "puncture wound" with said needle following injection and the high susceptibility of sustaining injury from the then-contaminated needle which can result in serious nosocomial disease. A sizable number of needle-stick injuries occur when cap replacement is implemented.

Certain preventive measures are now being taken which include the use of needle cutters which are utilized to cut the needle immediately following use. However, one of the shortcomings in this particular practice is the fact that blood from the cut needle is often splattered into the atmosphere which can possess significant risk in further contamination in the area. Cutting or snapping needles air mobilizes bacteria and is not recommended.

Also, a disposal unit has been devices wherein the needle is dropped into a container having a flexible top portion, supposedly preventing the further contact with the needle following disposal into the container. However, as the container becomes filled, needles would tend to accumulate at its opening and should an individual attempt to handle the container or make room for additional needles, the possibility is still present of being punctured with an old, used needle, again, therefore, being very susceptible to the contamination therefrom. It should also be noted that all hospital personnel, including housekeepers, lab personnel and medication administrators run the greatest risk of such injuries and disposal of such needles and subsequent expenses, should employees become injured or contaminated, is a serious problem within the health industry and must be addressed.

Several patents have been granted which show the use of a needle in the retracted position prior to injection, but it will be noted that none of the cited patents or any known use of syringes in the art, teach a needle which is retractable subsequent to the injection. These patents are noted as follows:

U.S. Pat. No. 2,880,725 issued to Kendall entitled "Syringes", shows the use of a syringe apparatus having a retractable needle. Although the apparatus does have a retractable needle on movement of the piston, the needle has become "locked" in place and is unable to be retracted back into the body following the injection.

U.S. Pat. No. 2,887,108 also issued to Kendall entitled "Syringes", teaches the use also of a retractable needle into the body of a syringe. However, again it fails to teach the idea of the needle being retracted following injection.

U.S. Pat. No. 2,737,950 issued to Berthiot entitled "Syringe For Hypodermic Injections" shows the use of a hypodermic needle which is retractable into the body of the syringe prior to injection. Again, the patent shows the use of a locking mechanism whereby the needle is locked into position once injection is addressed.

U.S. Pat. No. 3,527,216 issued to Snyder entitled "Hypodermic Syringe Assembly" is a patent relevant to the use of hypodermic syringe having mixing chambers therewithin for mixing more than one substance during injection.

U.S. Pat. No. 3,584,626 issued to Johanshon entitled "Hypodermic Syringe" relates to a hypodermic syringe having a retractable needle and inner syringe body with the inner syringe body imparting movement to the needle downward to the operable position. Again, no language in the patent shows the use of the needle being retracted back into the body following injection.

U.S. Pat. No. 3,828,775 issued to Armel entitled "Self-Packaged Hypodermic Syringe" again shows the use of a retractable needle except for the point portion which has a protective cap. This patent would fall short in the art in view of the fact that the cap is susceptible to being removed or misplaced, and the point of the needle is still available for inadvertent puncture of a handler of the needle following an injection.

U.S. Pat. Nos. 3,672,386 and 4,194,505 relate to a second embodiment of the apparatus having a containerized medication included in the syringe. These patents would be pertinent to the second embodiment of our invention, but again fall short of showing the retractable needle following an injection.

SUMMARY OF THE PRESENT INVENTION

The apparatus of the present invention solves the problems confronted in the present state of the art in a simple and straightforward manner. What is provided is a syringe apparatus having a syringe barrel open-ended on a first end for receiving a piston therewithin for movement down the syringe barrel, and having on the second end a constricted neck portion with a bore therethrough in communication with the area within the syringe barrel. There would be further provided a needle portion having an upper base for mounting the upper portion of the needle, with the needle slidable within the bore of the constricted neck portion, from a position retracted into the neck portion to a position movable out of the end of the neck portion for injection. There is further provided a first and second locking means. The first locking means allows locking engagement between the slidable piston within the barrel and the upper base portion of the needle, so that when in the locked position, the needle moves in relation with the piston portion. There is further provided a second locking means between the needle portion and the constricted neck portion of the barrel, so that the needle may be locked into injection position, i.e., the needle extruding out of the neck portion during use. Following the injection, the needle can be unlocked from the constricted neck portion and retracted back into the barrel for disposal, thus eliminating the hazard of an exposed contaminated needle.

In a second embodiment, the apparatus would include a needle portion locked into position within the constricted neck portion, with the piston withdrawn to the upper portion of the barrel containing medication therebetween. There would further be provided a cap portion for protection of the exposed needle prior to use of the apparatus. For use, the cap portion would be removed, the medication injected into the patient, and the needle portion, as with the preferred embodiment, unlocked from engagement with the neck portion and retracted back into the syringe for disposal.

Therefore, it is an object of the present invention to provide a syringe apparatus having a needle retracted into the barrel portion prior to and following use;

It is a further object of the present invention to provide a syringe apparatus wherein the needle may be locked into position for injection and unlocked for retracting following injection;

It is a further object of the present invention to provide an apparatus having a retractable needle prior to and following injection, containing medication within the apparatus as a self-contained unit.

In order to accomplish the above objects of the present invention, it is a principal feature of the present invention to provide a syringe having a needle portion movable from a retracted, unlocked position in relation to the barrel portion to an extruded, locked position for injection;

It is an additional feature of the apparatus to provide a barrel and needle portion engagable between locked and unlocked positions for movement of the needle from retractable to extended position for injection.

BRIEF DESCRIPTION OF THE DRAWINGS

For a further understanding of the nature and objects of the present invention, reference should be had to the following detailed description, taken in conjunction with the accompanying drawing, in which like parts are given like reference numerals and, wherein:

FIG. 1 is a cross-sectional view of the preferred embodiment of the apparatus of the present invention illustrating the needle in the retracted position within the barrel of the apparatus;

FIG. 2 is a cross-sectional view of the preferred embodiment of the apparatus of the present invention illustrating the needle in the retracted position and the plunger partially contained within the barrel of the apparatus;

FIG. 3 is a cross-sectional view of the preferred embodiment of the apparatus of the present invention illustrating the needle in the retracted position in locked engagement with the plunger portion of the apparatus within the barrel;

FIG. 4 is a cross-sectional view of the preferred embodiment of the apparatus of the present invention illustrating the needle in the extended position for injection in locked engagement with the barrel portion of the apparatus, with the plunger portion also in locked engagement with the needle portion (in phantom view) and in unlocked engagement and retracted back to the head of the barrel portion of the apparatus;

FIGS. 5A through 5C illustrate the receiving portion of the locking means of the preferred embodiment of the apparatus of the present invention;

FIGS. 6A and 6B illustrate the locking member of the preferred embodiment of the apparatus of the present invention; and FIGS. 7 and 8 illustrate an additional embodiment of the apparatus of the present invention.

DETAILED DESCRIPTION OF THE PREFERRED EMBODIMENT

FIGS. 1 through 6B illustrate the preferred embodiment of the syringe apparatus of the present invention as illustrated by the numeral 10. Beginning with FIG. 1, there is illustrated syringe apparatus 10 which comprises a typical barrel portion 12, which could be constructed of glass, plastic, or the like, having a continuous circular sidewall 14, open ended on a first end 16, for accommodating plunger 18 as seen in FIG. 2. Barrel portion 12 would also comprise flange shoulder portion 20 extending outwardly from its surface to provide a gripping means for the fingers of the operator during use of the apparatus. There is further provided on the second lower end portion of barrel 12 a constricted neck portion 22 terminating an end portion 24, with neck portion 22 providing an interior bore 26 of substantial circumference to slidably house needle 28 as it moves along bore 26 during use of the apparatus. As seen in the FIGURES, needle 28 would be a typical metal needle or the like having a bore 30 therewithin for allowing movement of medication therethrough prior to and during injection. In this particular apparatus, needle 28 provides an integral upper body portion 32 which, for the most part, comprises a flexible diaphragm 34 which abuts the inner wall 36 of barrel 12, creating a fluid-tight seal between the wall of diaphragm 34 and the inner wall 36 of barrel 12 during movement of the needle from retracted to unretracted positions.

As seen in FIGS. 1 through 4, apparatus 10 further provides a plurality of locking means allowing locking engagement between first plunger 18 and needle 32, and second between needle 32 and neck portion 22 of barrel 12. In describing the locking means, as is seen in the FIGURES, plunger 18 also comprises on its first end a shoulder member 40 for assisting in the movement of the plunger into and out of barrel 12 during use of the apparatus by the operator. On the second or lower end of plunger 18, there is also provided a second diaphragm portion 42, substantially identical to needle diaphragm portion 34, again in fluid-tight engagement between the inner wall 36 of barrel 12 and the wall of diaphragm 42, thus preventing fluid from leaking out of annular space 46 during use of the apparatus.

As was discussed earlier, both diaphragm 34 and 42 contain locking means, for locking engagement between the adjacent needle portion 32. As seen in the FIGURES, diaphragm 42 of plunger 18 has on its upper face a pair of extended T-locking members 48 which can be seen more clearly in FIG. 6B, having a base portion 50 engaged to the face of diaphragm 42 and a recessed transverse locking portions 53 and 55 mounted on base 54 locking engagement with the lower portion 32 which will be described further. As seen in the FIGURES, including FIGS. 5A through 5C, diaphragm portion 34 of needle 32 would comprise on its lower face locking recesses 53, 55 which would provide an opening 56 in substantial identical configuration with extended T-member 52 for accommodating extended T-member 52 therewithin. As seen in FIG. 3, plunger 18 has been moved into locked position against needle 32 with T-member 52 and diaphragm 42 inserted into recesses 53 and 55 of diaphragm 34 of needle 32. Following the insertion of transverse locking member 52 into recesses 53 and 55, plunger 18 is rotated clockwise approximately 30° and the flange portions 58 of transverse extended T-member 52 engagable in locked position within recesses 53,55. Of course, to disengage plunger 18 from needle 32, plunger 18 is likewise rotated counterclockwise for positioning extended transverse T-member 52 into openings 54 and 56 and for removal therefrom. In the operation of locking means, base 50 serves as a lock stop when plunger 18 is rotated, with the base 50 engaging the flange portion 58 of recesses 53 and 55, and both locking engagement and unlocking engagement of the apparatus.

As is further seen in the FIGURES, there is an identical set of locking members between needle 32 and neck portion 22 of barrel portion 12. As seen in FIG. 3, on its upper face of base portion 34 of needle 32, there is provided also a pair of T-locks 60 and 62 which, as seen in FIG. 4, are insertable into lock recesses 64 and 66 of neck portion 22. Again, like the locking system between plunger 18 and needle 32, and approximately 30° rotation of needle portion 32 following the insertion of extended T-member 60 and 62 into recesses 64 and 66, respectively, provides locking engagement between needle 32 and neck portion 22, thus needle 28, as seen in FIG. 4, is in locked engagement with neck 22 and in position for injection.

Also as seen in FIG. 4, following the locking of needle 28 in position, plunger 18 may be likewise rotated in the counterclockwise position, unlocked from needle 28, and retracted back into the upper portion of barrel 12 as will be described further.

OPERATION OF THE APPARATUS

A proper discussion of syringe apparatus 10 should include the complete operation of the apparatus as will be described. As seen in FIGS. 1 through 6B, syringe apparatus 10 could be packaged to include recessed needle portion 32 retracted into barrel portion 12 of apparatus 10 as seen in FIG. 1. It could also include plunger 18 inserted into the upper portion of barrel 12, although unlocked from needle portion 32 as seen in FIG. 2. Should one want to utilize the apparatus, it should be noted that needle 28 of needle portion 32 is completely retracted within barrel 12, and there is no access to the sharp point 29 of needle 28 prior to use, and following use, as will be described further. Upon utilizing apparatus 10, the operator would simply move plunger portion further inward into barrel 12, align transverse T-members 52 with the recess areas 53 and 55 respectively, rotate plunger 28 clockwise to place flange portions 58 of T-member 52 in locked engagement within recess 56 of diaphragm 34 of needle portion 32. Following this locked engagement, as seen in FIG. 3, between plunger 18 and needle portion 32, plunger 18 could be moved further inward so that retracted needle 28 is positioned extruding out from neck portion 24 of end portion 32 of barrel 12, and in position for injection. However, in positioning needle 28 in the proper position for injection, needle extended lock portions 60 and 62, as was previously discussed, would be aligned with recesses 64 and 66 in neck portion 22, likewise rotated clockwise, for locked engagement thereinto. Therefore, at this juncture in the operation, needle 28 is in position to receive medication from a source, whether it be a vial or the like.

As with a typical syringe, fluid medication is injected through orifice 30 of needle 28, by creating a vacuum with the movement of plunger 18 away from needle portion 32 thus drawing fluid up through port 30 as plunger 18 is retracted. This is well known in the art.

However, in this particular apparatus, in view of the fact that plunger 18 is in locked engagement with needle portion 32, plunger 18 must likewise be rotated counterclockwise in order to reposition flange members 58 of T-lock member in alignment with recessed openings 56, thus, when plunger member 18 is retracted needle portion 32 in locked engagement with neck portion 22 remains in position as seen in FIG. 4, plunger 18 being retracted and drawing medication into space 46 which could be defined as that space between the lower face portion of diaphragm 34 of needle portion 32, and the upper face of diaphragm 42 of plunger 18. Of course, in the art, syringe barrel 12 would be properly calibrated for signifying exactly the proper amount of fluid being drawn into space 46 for subsequent injection. Also, to assist in the alignment of the T-member with the locking recesses, demarcation lines could be provided on the wall of the diaphragm so that alignment of the demarcation lines indicated alignment of the locking means.

Following the drawing of fluid into space 46 for injection, the apparatus would be utilized as would be a typical hypodermic needle apparatus, with the needle 28 being inserted into the patient, and plunger 18 being moved inward forcing the fluid medication within space 46 through port 30 of needle 29 into the patient. Following the injection, plunger 42 would be in position as seen in phantom view in FIG. 4, i.e., adjacent diaphragm 34 of needle portion 32.

At this crucial point in the operation, plunger 18 is again placed in locked engagement with needle 32 as was described earlier, and upon counterclockwise rotation of needle portion 32, needle portion 32 is unlocked from base 22. Therefore, upon detraction of plunger portion 18, which is in locked engagement with needle portion 32, needle 28 is retracted back into the barrel 12 of the apparatus, as seen in FIG. 3, and therefore, is not available for inadvertent puncture of a patient, medication administrator or other ancillary personnel, and prevents the possible contamination of the victim therefrom. Therefore, the apparatus may be disposed of in whatever manner necessary, without the fear of having to come in contact with point 29 of needle 28 after disposal thereof.

FIG. 7 illustrates also the preferred embodiment of the apparatus, rather than containing the needle retracted into the apparatus as was seen in FIG. 1 prior to use, needle portion 32 would have needle 28 exposed exterior to neck 22, with, however, a cap portion 74 placed thereupon, thus allowing complete sterility of the needle prior to use. However, as with the preferred embodiment, following use of the needle after injection, the needle is again retracted back into the barrel 12 as seen in FIG. 3, plunger portion 18 removed as seen in FIG. 1, and can be disposed of. In either case, needle 28 is never exposed either prior to or after injection, and is therefore alleviated from causing and inadvertent sticking and possible contamination therefrom.

FIGS. 7 and 8 illustrate an additional embodiment of the apparatus of the present invention. As seen in the figures, this particular embodiment of the apparatus would enable the apparatus to be marketed with the fluid medication 70 self-contained within barrel 12 upon receipt of the apparatus. As seen in FIG. 8, again, there would be provided a plunger 18 contained within barrel 12 of the apparatus, with plunger 18 threadably engagable to diaphragm 42 via threaded portion 72 during use. This would be so in order to accommodate the shipment of the apparatus, so that upon receipt of the apparatus, plunger portion 18 could be threadably engaged into diaphragm 42 for use thereafter rather than extruding from the top portion of barrel 12 as seen in FIG. 8. Likewise, there would be provided needle portion 32 as seen in FIG. 8 in locked engagement with lower portion 22, with needle 28 extruding from the neck 24 of neck portion 22. However, in order to prevent the inadvertent sticking of a patient, medication administrator or other ancillary personnel prior to injection, and in order to maintain needle 28 in a sterile condition, there is provided cap portion 74 which would threadably engage neck 24 and would be removable upon use of the apparatus.

As with the preferred embodiment, in utilizing the apparatus, cap portion 74 would be threadably removed from the neck portion 24, thus exposing needle 28. In view of the fact that the medication has already been measured and contained within barrel 12 between diaphragm 32 and 42, the needle would simple be inserted into the patient, plunger 18 moved into the position forcing the fluid out through port 30 of needle 28, and following the injection, as would the preferred embodiment, plunger 18 would be rotated to disengage needle portion 32 from neck portion 22 and retract needle portion 32 back into barrel 12 as seen in FIG. 3 in the preferred embodiment disengage plunger 18 and remove as seen in FIG. 1. The principal feature of this second embodiment is the fact that the medication is self-contained within barrel 12, thus preventing the necessity of having a measured quantity of medication drawn into the apparatus. Also, as with the novel features of the preferred embodiment, the needle can be placed from a locked to an unlocked position and retracted back into barrel 12 following use of the apparatus, thus preventing the possible inadvertent post-injection sticking of an individual and subsequent contamination therefrom.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A syringe apparatus, which comprises:
  a. a substantially cylindrical barrel portion;
  b. a needle portion, at least partially contained within said hollow barrel bore portion, and at times partially extruding therefrom;
  c. a plunger portion insertable in the second end of said barrel portion then movable within said barrel portion;
  d. means for engaging and disengaging said needle portion to said plunger portion, so that in the engaged position, said needle portion moves in unison with said plunger portions;
  e. means for engaging said needle portion to the first end of said barrel portion, so that in the engaged position, the point of said needle portion is extruding from said plunger portion and fixedly attached thereto; and
  f. means for disengaging said needle portion from said barrel portion and retracting said needle completely into the hollow of said barrel portion.

2. The apparatus in claim 1, wherein said needle portion further comprises a diaphragm fixedly attached to said needle, said diaphragm having a locking member on the upper and lower portion.

3. The apparatus in claim 1, wherein said plunger portion further comprises a diaphragm having a locking member on the upper portion of said diaphragm.

4. The apparatus of claim 1 wherein said barrel portion further comprises a locking member on the first end of said barrel portion for locking engagement with the upper locking member of said needle portion.

5. The apparatus of claim 3 wherein said lower locking member of said needle portion moves into a locking engagement with a upper locking member of said plunger.

6. A method of retracting the needle of the hypodermic syringe following injection, comprising the following steps:
  a. providing a hypodermic syringe having a substantially cylindrical hollow barrel portion, open ended on at least one end;
  b. providing a needle member movable between retracted and unretracted positions within said barrel portions;
  c. providing a plunger portion insertable into the hollow of said barrel portion movable within said barrel portion;
  d. providing locking means for engaging or disengaging said needle portion to said barrel portion and said plunger portion to said needle portion;
  e. inserting said plunger portion into said barrel portion;
  f. lockingly engaging said plunger portion to said needle portion;
  g. moving said plunger portion and said locked needle portion in relation to said barrel portion so that the point of said needle portion extrudes from said barrel portion;
  h. lockedly engaging said needle portion to said barrel portion;
  i. disengaging said plunger portion from said needle portion;
  j. preparing said needle portion and said plunger portion for injecting into fluid to be administered;
  k. injecting said needle portion into the fluid to be administered;
  l. retracting said plunger portion from said locked needle portion, thus drawing fluid into the area between said needle portion and said plunger portion
  m. retrieving said needle portion from said fluid and injecting into the patient to be injected;
  n. plunging said plunger portion into a position adjacent said needle portion; thus forcing said fluid into said patient;
  o. lockingly engaging said plunger portion to said needle portion;
  p. disengaging said needle portion from said barrel portion; and
  q. retracting said needle locked to said plunger to said barrel portion until the entire needle portion is retracted into said barrel portion.

7. The method in claim 6, further comprising the step of removing said plunger portion from said barrel portion following the retraction of said needle into said barrel portion.

8. The method in claim 6, further comprising the step of dispensing with said apparatus following the retraction of said needle portion back into said barrel portion.

* * * * *

UNITED STATES PATENT AND TRADEMARK OFFICE
CERTIFICATE OF CORRECTION

PATENT NO. : B1 4,507,117

DATED : June 21, 1988

INVENTOR(S) : VINING, HERBERT C./RYAN, CLARA G.

It is certified that error appears in the above-identified patent and that said Letters Patent is hereby corrected as shown below:

THE DATE OF ISSUANCE OF THE ORIGINAL PATENT AS SHOWN ON THE REEXAMINATION CERTIFICATE SHOULD BE CHANGED TO --MARCH 26, 1985.--

Signed and Sealed this

Twenty-first Day of March, 1989

Attest:

DONALD J. QUIGG

*Attesting Officer*  *Commissioner of Patents and Trademarks*

REEXAMINATION CERTIFICATE (872nd)

United States Patent [19]

Vining et al.

[11] B1 4,507,117
[45] Certificate Issued   Jun. 21, 1988

[54] SYRINGE APPARATUS WITH RETRACTABLE NEEDLE

[76] Inventors: Herbert C. Vining, R.R. 1, Box 339 HV; Clara G. Ryan, R.R. 1, Box 399 FG, both of Patterson, La. 70392

Reexamination Request:
No. 90/001,214, Apr. 13, 1987

Reexamination Certificate for:
Patent No.: 4,507,117
Issued: May 26, 1985
Appl. No.: 512,272
Filed: Jul. 11, 1983

[51] Int. Cl.⁴ .................. A61M 5/32; A61M 5/315
[52] U.S. Cl. ................................................ 604/196
[58] Field of Search ............ 604/194, 195, 196, 197, 604/198, 218, 228, 229, 231

[56]           References Cited
       U.S. PATENT DOCUMENTS 2,722,215  11/1955  Dahlgren ................ 604/157
2,880,725   4/1959  Kendall ................. 604/196
3,487,834   1/1970  Smith, Jr. et al. ..... 604/117
4,026,287   5/1977  Haller .................. 604/195

*Primary Examiner*—J. Yasko

[57] ABSTRACT

A syringe apparatus having a syringe barrel open-ended on a first end for receiving a piston therewithin for movement down the syringe barrel, and having on the second end a constricted neck portion with a bore therethrough in communication with the bore within the syringe barrel. There would be further provided a needle portion having an upper base for mounting the upper portion of the needle, with the needle slidable within the bore of the constricted neck portion, from a position retracted into the neck portion to a position movable out of the end of the neck portion for injection. There is further provided a first and second locking members. The first locking member allows locking engagement between the slidable piston within the barrel and the lower base portion of the needle, so that when in the locked position the needle moves in relation with the piston portion. There is further provided a second locking member between the needle portion and the constricted neck portion of the barrel, so that the needle may be locked into injection position, i.e., the needle extruding out of the neck portion during use. Following the injection, the needle can be unlocked from the constricted neck portion and retracted back into the barrel for disposal, thus eliminating the hazard of an exposed contaminated needle, further extraction of the plunger portion from the syringe prior to disposal of same.

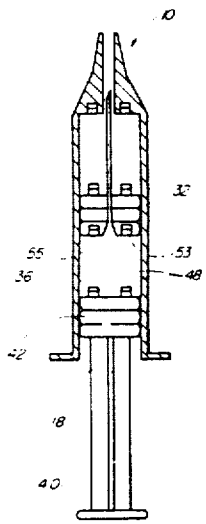

B1 4,507,117

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–8 are determined to be patentable as amended.

New claims 9 and 10 are added and determined to be patentable.

1. A *disposable safety* syringe apparatus, which comprises:
   a. a substantially cylindrical barrel portion *having a hollow bore therein;*
   b. a needle portion, at least partially contained *and* moveable within *the bore of* said [hollow] barrel [bore] portion, [and at times] *between positions* partially extruding [therefrom] *from a first end thereof and wholly contained therein;*
   c. a plunger portion [insert] *insertable* in the second end of said barrel portion [then] *and* movable within *the bore of* said barrel portion *for moving fluid through the bore of said barrel portion;*
   d. means [for engaging and disengaging] *adapted for and capable of selectively locking and unlocking* said needle portion to said plunger portion, *during use thereof,* so that in the [engaged] *locked* position, said needle portion moves in unison with said plunger [portions] *portion;*
   e. means [for engaging] *adapted to and capable of selectively locking* said needle portion to [in] *the barrel portion at* the first end of said barrel portion so that in the [engaged] *locked* position the point of said needle portion is extruding from said [plunger] *barrel* portion and fixedly attached thereto;
   f. means [for disengaging] *adapted to and capable of selectively unlocking* said needle portion from said barrel portion and retracting said needle *portion* completely into the hollow *bore* of said barrel portion *for storage therein.*

2. The apparatus [in] *in* claim 1, wherein said needle portion further comprises a diaphragm fixedly attached to said needle, [said diaphragm having a locking member on the upper and lower portion] *said plunger portion further comprises a diaphragm, and said means for locking and unlocking said needle portion with said plunger portion further comprises releasable cooperative locking members on upper and lower portions of the diaphragms of the plunger portion and the needle portion, respectively.*

3. The apparatus [in] *of* claim [1] *2,* wherein said [plunger] *needle* portion further comprises a diaphragm [having a locking member on the upper portion of said diaphragm] *fixedly attached to said needle, and said means for locking said needle portion to said barrel portion and said means for unlocking said needle portion from said barrel portion further comprise releasable cooperative locking members on the barrel portion proximate the first end of said barrel portion and on an upper portion of the diaphragm of said needle portion.*

4. The apparatus of claim [1] *2,* wherein [said barrel portion further comprises a locking member on the first end of said barrel portion for locking engagement with the upper locking member of] *said needle portion further comprises a diaphragm fixedly attached to said needle, said plunger portion further comprises a diaphragm fixedly attached to a plunger extending out of said second end of said barrel portion, said means for locking and unlocking said needle portion with said plunger portion further comprises releasable cooperative locking members on upper and lower portions of the diaphragms of the plunger portion and the needle portion, respectively, and said means for locking said needle portion to the barrel portion and said means for unlocking said needle portion from said barrel portion further comprises releasable cooperative locking members on the barrel portion proximate the first end of said barrel portion and on an upper portion of the diaphragm of said needle portion.*

5. The apparatus of claim 3, wherein said [lower locking member of said needle portion moves into a locking engagement with a upper locking member of said plunger] *cooperative locking members further comprise protruding tabs and recessed slots that are lockable and unlockable responsive to relative rotation of the said locking members about an axis of the bore of the barrel portion.*

6. [A method of retracting the needle of the hypodermic syringe following injection, comprising the following steps] *An improved method for injecting a patient with fluid, comprising the following steps:*
   a. providing a hypodermic syringe having a substantially cylindrical hollow barrel portion, open ended on at least one end;
   b. providing a needle [member] *portion which is* movable between retracted and unretracted positions within said barrel [portions] *portion;*
   c. providing a plunger portion insertable into the hollow of said barrel portion *and* movable within said barrel portion;
   d. providing locking means for [engaging] *locking* or [disengaging] *unlocking* said needle portion to said barrel portion and said plunger portion to said needle portion;
   e. inserting said plunger portion into said barrel portion;
   f. lockingly engaging said plunger portion to said needle portion;
   g. moving said plunger portion and [said] *the* locked needle portion in relation to said barrel portion so that the point of said needle portion extrudes from said barrel portion;
   h. lockedly engaging said needle portion [to] *with* said barrel portion;
   i. [disengaging] *unlocking* said plunger portion from said needle portion;
   j. preparing said needle portion and said plunger portion for injecting into fluid to be administered;
   k. injecting said needle portion into the fluid to be administered;
   l. retracting said plunger portion from said locked needle portion, thus drawing fluid into the area between said needle portion and said plunger portion;

m. retrieving said needle from said fluid and injecting it into the patient to be injected;
n. plunging said plunger portion into a position adjacent said needle portion[;] , thus forcing said fluid into said patient;
o. lockingly engaging said plunger portion [to] *with* said needle portion;
p. [disengaging] *unlocking* said needle portion from said barrel portion; and
q. retracting said needle *portion* locked to said plunger [to] *into* said barrel portion until the entire needle portion is retracted into said barrel portion.

7. The method [in] *of* claim 6, further comprising the step of removing said plunger portion from said barrel portion following the retraction of said needle *portion* into said barrel portion.

8. The method [in] *of* claim 6, further comprising the step of dispensing with [said apparatus] *the syringe* following the retraction of said needle portion back into said barrel portion.

9. A disposable safety syringe apparatus, which comprises:
   a. a substantially cylindrical barrel portion having a hollow bore therein;
   b. a needle portion, at least partially contained and moveable within the bore of said barrel portion, between positions partially extruding from a first end thereof and wholly contained therein;
   c. a plunger portion insertable in the second end of said barrel portion and movable within the bore of said barrel portion for moving fluid through the bore of said barrel portion;
   d. means adapted for and capable of repetitively and selectively locking and unlocking said needle portion to said plunger portion, during use thereof, so that in the locked position, said needle portion moves in unison with said plunger portion;
   *e. means adapted to and capable of repetitively and selectively locking said needle portion to the barrel portion at the first end of said barrel portion so that in the locked position the point of said needle portion is extruding from said barrel portion and fixedly attached thereto;*
   *f. means adapted to and capable of repetitively and selectively unlocking said needle portion from said barrel portion and retracting said needle portion completely into the hollow bore of said barrel portion for storage therein.*

*10. A disposable safety syringe apparatus, which comprises:*
   *a. a substantially cylindrical barrel portion having a hollow bore therein;*
   *b. a needle portion, at least partially contained and moveable within the bore of said barrel portion, between positions partially extruding from a first end thereof and wholly contained therein;*
   *c. a plunger portion insertable in the second end of said barrel portion and movable within the bore of said barrel portion for moving fluid through the bore of said barrel portion;*
   *d. means adapted for and capable of repetitively locking and unlocking said needle portion to said plunger portion, during use thereof, so that in the locked position, said needle portion moves in unison with said plunger portion;*
   *e. means adapted to and capable of repetitively locking said needle portion to the barrel portion at the first end of said barrel portion so that in the locked position the point of said needle portion is extruding from said barrel portion and fixedly attached thereto;*
   *f. means adapted to and capable of repetitively unlocking said needle portion from said barrel portion and retracting said needle portion completely into the hollow bore of said barrel portion for storage therein.*

* * * * *